(12) United States Patent
Fuimaono et al.

(10) Patent No.: US 9,668,704 B2
(45) Date of Patent: Jun. 6, 2017

(54) METHOD AND DEVICE FOR VISUALLY ASSISTING AN ELECTROPHYSIOLOGICAL USE OF A CATHETER IN THE HEART

(75) Inventors: Kristine Fuimaono, West Berlin, NJ (US); Gal Hayam, Tivon (IL); Yuval Karmi, Hadera (IL); Reinmar Killmann, Forchheim (DE); Assaf Preiss, Bet Yizhaq (IL); Norbert Rahn, Forchheim (DE); Frank Sauer, Princeton, NJ (US); Chenyang Xu, Allentown, NJ (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 787 days.

(21) Appl. No.: 10/569,957

(22) PCT Filed: Aug. 24, 2004

(86) PCT No.: PCT/EP2004/009446
§ 371 (c)(1),
(2), (4) Date: Nov. 30, 2006

(87) PCT Pub. No.: WO2005/027766
PCT Pub. Date: Mar. 31, 2005

(65) Prior Publication Data
US 2007/0287902 A1 Dec. 13, 2007

(30) Foreign Application Priority Data
Sep. 1, 2003 (DE) .................................. 103 40 546

(51) Int. Cl.
*A61B 5/05* (2006.01)
*A61B 6/03* (2006.01)
(Continued)

(52) U.S. Cl.
CPC .............. *A61B 6/032* (2013.01); *A61B 5/055* (2013.01); *A61B 8/14* (2013.01); *A61B 5/7285* (2013.01);
(Continued)

(58) Field of Classification Search
CPC ........................... A61B 19/5244; A61B 5/055
(Continued)

(56) References Cited

U.S. PATENT DOCUMENTS

| 5,526,812 A | 6/1996 | Dumoulin et al. |
| 5,687,737 A | 11/1997 | Branham et al. |

(Continued)

FOREIGN PATENT DOCUMENTS

| DE | 195 42 605 A1 | 5/1996 |
| DE | 196 21 540 A | 1/1997 |

(Continued)

OTHER PUBLICATIONS

International Search Report (PCT/ISA/210).
(Continued)

*Primary Examiner* — Tse Chen
*Assistant Examiner* — Hien Nguyen
(74) *Attorney, Agent, or Firm* — Notaro, Michalos & Zaccaria P.C.

(57) ABSTRACT

The invention relates to a device and to a method for visual assistance during the electrophysiological use of a catheter in the heart, enabling electroanatomic 3D mapping data relating to an area of the heart to be treated to be visualized during the use of the catheter. Before the catheter is used, 3D image data of a body region containing the area to be treated is detected by means of a method for tomographic 3D imaging. The area to be treated or significant parts thereof are extracted from said 3D image data, in order to obtain selected 3D image data. The electroanatomic 3D mapping
(Continued)

data and the selected 3D image data obtained are then classed in terms of position and dimension, and are adjacently visualized, for example, during the catheter ablation. The inventive method and associated device enable the orientation of the operator to be improved during the use of a catheter in the heart.

14 Claims, 1 Drawing Sheet

(51) Int. Cl.
*A61B 5/055* (2006.01)
*A61B 8/14* (2006.01)
*A61B 5/00* (2006.01)
*A61B 6/00* (2006.01)
*A61B 8/00* (2006.01)
*A61B 18/14* (2006.01)
*A61B 18/00* (2006.01)
*G01R 33/56* (2006.01)

(52) U.S. Cl.
CPC ............ *A61B 6/541* (2013.01); *A61B 8/543* (2013.01); *A61B 18/1492* (2013.01); *A61B 2018/00375* (2013.01); *A61B 2018/00839* (2013.01); *G01R 33/5608* (2013.01)

(58) Field of Classification Search
USPC ........................................................ 600/406
See application file for complete search history.

(56) References Cited

U.S. PATENT DOCUMENTS

| | | | |
|---|---|---|---|
| 6,058,218 A | 5/2000 | Cline | |
| 6,128,002 A * | 10/2000 | Leiper | 345/156 |
| 6,144,875 A * | 11/2000 | Schweikard et al. | 600/427 |
| 6,308,097 B1 | 10/2001 | Pearlman | |
| 6,509,915 B2 | 1/2003 | Berman et al. | |
| 6,556,695 B1 * | 4/2003 | Packer et al. | 382/128 |
| 6,563,941 B1 | 5/2003 | O'Donnell et al. | |
| 6,572,476 B2 | 6/2003 | Nagakura | |
| 6,574,629 B1 | 6/2003 | Cooke, Jr. et al. | |
| 6,711,433 B1 | 3/2004 | Geiger et al. | |
| 6,771,262 B2 * | 8/2004 | Krishnan | 345/424 |
| 6,865,248 B1 | 3/2005 | Rasche et al. | |
| 6,937,750 B2 | 8/2005 | Natanzon et al. | |
| 7,233,340 B2 * | 6/2007 | Hughes et al. | 345/629 |
| 2001/0036303 A1 * | 11/2001 | Maurincomme et al. | 382/132 |
| 2001/0055016 A1 | 12/2001 | Krishnan | |
| 2002/0065456 A1 | 5/2002 | Bazin et al. | |
| 2002/0087329 A1 * | 7/2002 | Massaro et al. | 704/275 |
| 2002/0176608 A1 * | 11/2002 | Rose | 382/108 |
| 2003/0004405 A1 | 1/2003 | Townsend et al. | |
| 2003/0018251 A1 | 1/2003 | Solomon | |
| 2003/0153907 A1 | 8/2003 | Suorsa et al. | |
| 2003/0187358 A1 | 10/2003 | Okerlund et al. | |
| 2004/0029068 A1 | 2/2004 | Sachdeva et al. | |
| 2004/0170309 A1 | 9/2004 | Hughes et al. | |
| 2004/0233217 A1 | 11/2004 | Chiu et al. | |
| 2007/0055142 A1 * | 3/2007 | Webler | 600/425 |

FOREIGN PATENT DOCUMENTS

| | | |
|---|---|---|
| DE | 19621540 | 1/1997 |
| DE | 199 53 308 A1 | 6/2000 |
| DE | 19953308 A1 * | 6/2000 |
| DE | 100 47 314 A1 | 4/2001 |
| EP | 0 945 104 A | 9/1999 |
| EP | 0945104 | 9/1999 |
| EP | 1 182 619 A2 | 2/2002 |
| JP | 9006986 A | 1/1997 |
| JP | 2001070269 A | 3/2001 |
| JP | 2001340336 A | 12/2001 |
| JP | 200279425 | 12/2002 |
| JP | 2002345725 A | 12/2002 |
| JP | 2003517361 T | 5/2003 |
| WO | WO 00/25672 | 5/2000 |
| WO | WO 00/25672 A | 5/2000 |
| WO | WO 02/062265 A2 | 8/2002 |

OTHER PUBLICATIONS

International Preliminary Examination Report (PCT/IPEA/409 and PCT/IPEA/416).
German Translation Aid.
Paul F.Hemler et al.: <<A System for Multimodality Image Fusion>>. Seventh Annual IEEE Symposium on Computer-Based Medical Systems, 1994, SA5: Image Processing 4, pp. 335-340
ET van der Velde et al.: "Fusion of Electrophysiology Mapping Data and Angiographic Images to Facilitate Readiofrequency Ablation", in: Computers in Cardiology, vol. 27, 2000, pp. 85-87.
S.Kewitz et al.: "A New Method of Cardiac Activation Mapping: an Experimental Study", in: Computers in Cardiology, vol. 27, 2000, pp. 509-512.
Dorin Panescu et al.: "Electro-anatomical Four-dimensional Mapping of Ventricular Tachycardia", Proceedings of the 23$^{rd}$ Annual EMBS International Conference, Oct. 25-28, 2001, Turkey, pp. 405-407.
International Search Report and German Office Action.
K. Watabe. "Multi-modality Image Registration and Superposition", Japanese Society of Radiological Technology, Academic Journals, Jan. 2003, vol. 59, No. 1, 60-65; Others; 2003; with English translation.
Notification of Reasons for Refusal (Office Action) for Japanese patent application No. 2006-525075 mailed Mar. 2, 2010 with English translation.
Japanese Office Action and English translation thereof dated Apr. 30, 2009.

* cited by examiner

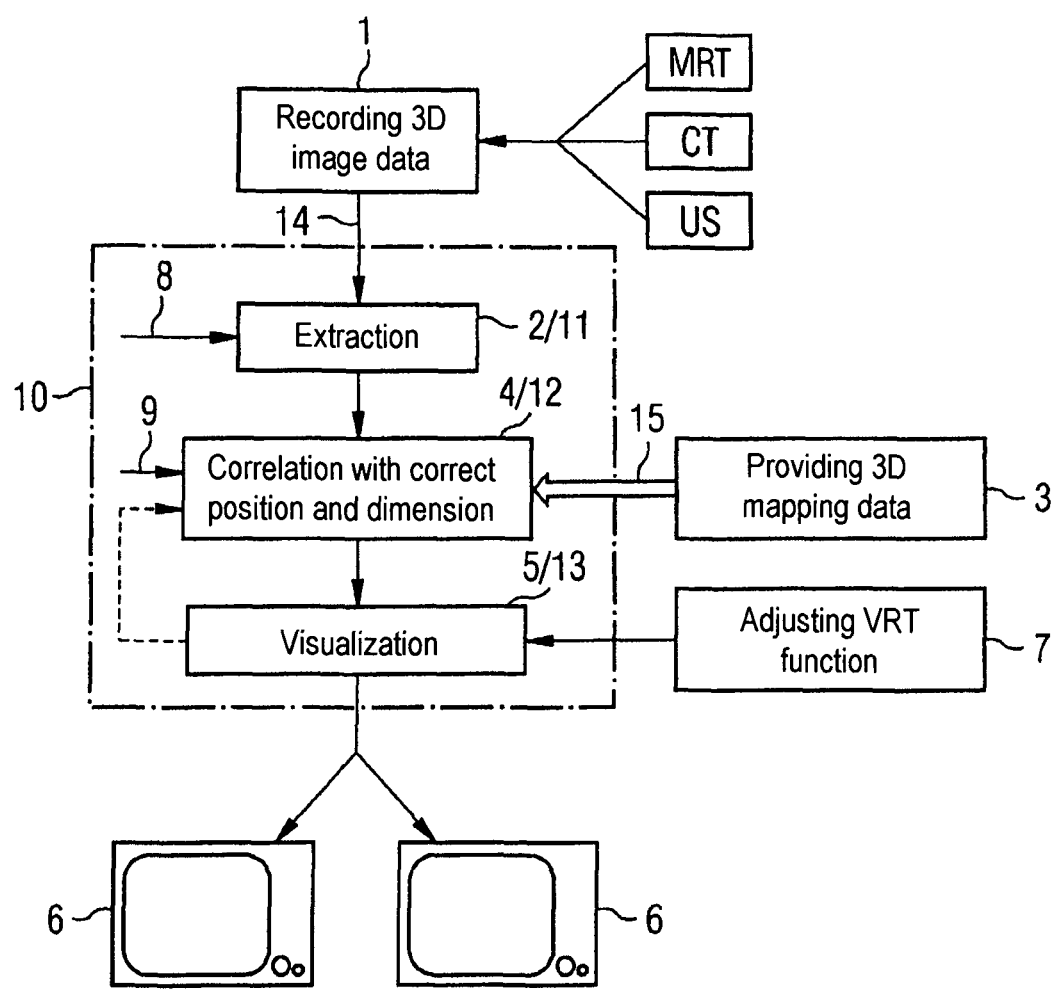

METHOD AND DEVICE FOR VISUALLY ASSISTING AN ELECTROPHYSIOLOGICAL USE OF A CATHETER IN THE HEART

This application is the national phase under 35 U.S.C. §371 of PCT International Application No. PCT/EP2004/009446 which has an International filing date of Aug. 24, 2004, which designated the United States of America and which claims priority on German Patent Application number 103 40 546.1 filed Sep. 1, 2003, the entire contents of which are hereby incorporated herein by reference.

FIELD

The present invention generally relates to a method and/or to a device for visually supporting an electrophysiology catheter application in the heart. For example, it may relate to one whereby electroanatomical 3D mapping data of an area of the heart to be treated, which are provided during the performance of catheter application, are visualized.

BACKGROUND

The treatment of cardiac arrhythmia has changed considerably since the introduction of the technology of catheter ablation by way of high-frequency current. In this technology, an ablation catheter is introduced into one of the heart chambers via veins or arteries under X-ray control and the tissue causing the cardiac arrhythmia is removed by high-frequency current.

The prerequisite for performing a catheter ablation successfully is that the cause of the cardiac arrhythmia is accurately located in the heart chamber. This locating is done via an electrophysiological investigation during which electrical potentials are detected spatially resolved with a mapping catheter introduced into the heart chamber. This electrophysiological investigation, the so-called electroanatomical mapping, thus provides 3D mapping data which can be displayed on a monitor. In many cases, the mapping function and the ablation function are combined in one catheter so that the mapping catheter is also an ablation catheter at the same time.

A known electroanatomical 3D mapping method such as can be performed by way of the carto system by the company Biosense Webster Inc., USA, is based on electromagnetic principles. Underneath the examining table, three different low-intensity alternating magnetic fields are built up. Using integrated electromagnetic sensors at the catheter point of the mapping catheter, it is possible to measure the voltage changes induced by catheter movements within the magnetic field and to calculate the position of the mapping catheter at any time with the aid of mathematical algorithms. Probing the endocardial contour of a heart chamber point by point with the mapping catheter and simultaneously detecting the electrical signals produces an electroanatomical three-dimensional map in which the electrical signals are reproduced color coded.

As a rule, the orientation of the operator required for guiding the catheter has hitherto been effected via fluoroscopic visualization. Since, in electroanatomical mapping, the position of the mapping catheter is known at any time with this technology, the orientation can also take place by continuous representation of the catheter point in the electroanatomical map after a sufficiently large number of measuring points has been detected, so that fluoroscopic imaging technology with X-ray screening can be omitted at this stage.

A fundamental problem in performing the catheter ablation inside the heart is that it has hitherto not been possible to provide optimal orientation of the operator during the guidance of the catheter. A more accurate representation of the morphological environment during the guidance of the catheter which, on the one hand, increase the accuracy during the catheter ablation and, on the other hand, of shortening the time for performing the electroanatomical mapping. Furthermore, the X-ray screening still required for the electroanatomical mapping in many cases could be reduced or avoided in that the X-ray dose applied could also be reduced.

To improve the orientation of the operator when guiding the catheter, different techniques are known. In one technique, a special catheter with an ultrasonic probe is used as is offered, for example, by company Siemens AG Medical Solutions under the title Acunav. Parts of the target tissue to be removed, together with the catheter, can be visualized in real-time via a two-dimensional ultrasonic detection of the environment and of a part of the catheter. However, using such a catheter does not supply three-dimensional image information. The ultrasonic representation can only be used, therefore, in order to insert, for example, a so-called loop catheter into the opening of the pulmonary vein. After the loop catheter has been positioned, tissue removal around the opening of a pulmonary vein can be performed by visualizing both the loop catheter and the ablation catheter by way of X-radiation.

In another known technique, a loop catheter is placed at the opening of the pulmonary vein without the support of imaging 2D ultrasonic technology by applying a contrast medium via a catheter placed in the left atrium in the area of the pulmonary vein opening under X-ray screening. During this process, the contrast medium becomes distributed and a small proportion leaves with the blood flow via the pulmonary vein. This short-time visualization of the pulmonary vein enables the loop catheter to be placed in the opening. The catheter ablation can then be performed as with the above-mentioned technique.

A technique is also known in which the opening of the pulmonary vein is located by electroanatomical mapping of the left atrium and of the pulmonary veins by first introducing the mapping catheter into the pulmonary vein and then pulling it back until electrical activity of the atrium is detected. This position corresponds to the position of the opening of the pulmonary vein around which the target tissue is to be removed.

SUMMARY

It is an object of at least one embodiment of the present invention to specify a method and a device for visually supporting an electrophysiology catheter application in the heart which provides for, for example, improved orientation during the guidance of the catheter during the catheter application, particularly in electroanatomical mapping and/or during a catheter ablation.

In the present method of at least one embodiment, for visually supporting an electrophysiology catheter application in the heart, particularly a catheter ablation, 3D image data of a body region containing the area to be treated are first recorded by way of a tomographical 3D imaging method before the catheter application is carried out. The area to be treated, or at least significant portions of it, is then extracted from the 3D image data. The resultant selected 3D image data and the electroanatomical 3D mapping data provided are finally correlated in the correct position and dimension and, preferably while the catheter application is being performed, are visualized next to one another at the same time in the correct position and dimension.

At least one embodiment of the present method and/or the associated device thus provide the operator with assistance for orientation within the heart by showing the anatomical 3D image data and the 3D mapping data next to one another with the same orientation and scaling on one or more display panels or monitors. This makes it possible to identify both the electrophysiological properties of the tissue and the associated anatomical environment in real time during the catheter application. In this context, the visualization can be provided both in the control room and in the workroom in the cardiac catheter laboratory.

For recording the 3D image data, methods of X-ray computer tomography, of magnetic resonance tomography or of 3D ultrasonic imaging can be used, for example. Combinations of these imaging methods are also possible, of course. It is only necessary to pay attention to the fact that the 3D image recordings take place in the same heart phase as the electroanatomical 3D mapping data provided so that in each case the same state of the heart is observed. This can be ensured with the familiar technology of ECG gating during the recording of the image data and of the electro-anatomical mapping data.

Correlating the electroanatomical 3D mapping data with the selected 3D image data in the correct dimension and position can be done by way of different techniques. One possibility resides in registration between the respective data by visually matching a 3D surface profile extracted by segmentation with the representation of the electroanatomical 3D mapping data. Furthermore, artificial markers or natural distinct points can be used which can be recognized in both records. Apart from the area to be treated, a neighboring area can also be used for the registration if it is contained in the existing data.

In an advantageous embodiment of the method and/or of the device, the registration takes place in a first stage in which only a relatively small portion of the electroanatomical 3D mapping data is present, with the aid of artificial markers or of distinct points, and in one or more subsequent stages in which a greater number of electroanatomical 3D mapping data is already present, by surface matching. In this manner, the registration is improved with the increasing number of electroanatomical 3D mapping data during the catheter application.

The selected 3D image data can be represented by way of a volume rendering technique. In a further embodiment, an extracted 3D surface profile is represented by a polygonal grid as is known from the field of computer graphics. The representation can be performed with an adjustable volume-rendering transfer function.

At least one embodiment the present device for performing at least one embodiment of the method includes one or more input interfaces for the electroanatomical 3D mapping data and the 3D image data recorded by means of an imaging tomographic method. The device has an extraction module for extracting an area which is to be treated, or significant portions of it, from the 3D image data, said extraction module providing selected 3D image data. This extraction module is connected to a registration module which is designed for correlation of the electroanatomical 3D mapping data and the selected 3D image data in the correct position and dimension. This registration module, in turn, is connected to a visualization module which provides the 3D mapping data and the selected 3D image data for visualization such that they can be shown in the correct position and dimension next to one another using one or more display units.

The individual modules of the device are constructed in different embodiments corresponding to the performance of the different embodiments of the method described in the text which follows.

In the text which follows, an embodiment of the present method and associated device will again be explained in greater detail in connection with the FIGURE. For this purpose, the FIGURE shows the individual steps in the performance of an embodiment of the present method and individual modules of the associated device, respectively.

In a first step 1 in an embodiment of the present method, the 3D image data of the body region which particularly contains the heart chamber to be treated are recorded. During the recording of these 3D image data, a larger part of the heart can also be included for a later registration. The 3D image data are recorded by way of a method of tomographic 3D imaging such as, for example, X-ray computer tomography, magnetic resonance tomography or 3D ultrasonic techniques. During the recording of the 3D image data, care must be taken that these image data are in each case recorded for the same heart phase for which the electroanatomical 3D mapping data will also be provided later. This is ensured by ECG gating of the image recording and recording of the 3D mapping data, for example by referring to a percentage of the RR interval or to a fixed time interval before or after the R peak.

During the performance of an embodiment of the method, it is of importance to record high-resolution image data of the heart chamber which is electroanatomically measured during the catheter application. Preferably, a contrast medium in association with a test bolus or bolus tracking is therefore used for recording the 3D image data.

As a rule, electrophysiological procedures are performed in one of the heart chambers, so that 3D mapping data from the heart chamber to be treated are provided. In an embodiment of the present application, heart chambers are to be understood as both ventricles and atria. For visualization in line with an embodiment of the present method, the image data from this heart chamber, or at least significant portions of it, are extracted from the recorded 3D image data. For extraction step it is possible to use the following techniques or else a combination of these techniques.

In one refinement of an embodiment of the method, extraction 2 can be performed by way of "volume clipping". This involves interactively using an input interface 8 to make successive settings for a number of clip levels, which limit a 3D image available from the 3D image data to a subvolume which contains the heart chamber to be treated.

Another possible technique for extraction 2 involves "volume punching", in which successive punching operations are performed interactively in order to mask out irrelevant parts of the 3D image available from the 3D image data. This may also concern parts of the heart which are not relevant to the later representation.

Another technique involves segmenting the 3D image data in order to obtain a 3D surface profile of the heart chamber in question and optionally of vessels adjacent to it. This segmentation can be used for later representation of the surface profile of these objects and, in one advantageous refinement of an embodiment of the method, also for correlation with the 3D mapping data in the correct position and dimension.

The segmentation of the heart chamber to be treated—or other chambers or heart vessels—can take place in the form of a 2D segmentation in individual layers. One possibility resides in performing a fully automatic segmentation of all layers of the heart chamber obtained by an embodiment of the imaging method. As an alternative, one or more of the layers can also be segmented interactively by an operator and the layers following in each case can be segmented automatically on the basis of the prior knowledge of the layers already segmented. The interactive segmentation of individual layers can also be supported by semiautomatic techniques such as, for example the technique of active contours. After the segmentation of all individual layers, the 3D surface profile of the heart chamber can then be reconstructed.

The segmentation can also take place as 3D segmentation of the heart chamber to be treated—or of other chambers or heart vessels—by way of known 3D segmentation techniques. Examples of such 3D segmentation techniques are the threshold technique or the technique of region growing. If these fully automatic 3D segmentation algorithms do not work reliably in individual cases, an interactive input capability for an operator can be provided in order to be able to specify, for example, gray scale thresholds or spatial blockers.

Extraction 2 is performed in the extraction module 11 of the present device 10. This extraction module 11 receives the recorded 3D image data via an appropriate input interface 14. In the same way, the device 10 is supplied with the 3D mapping data via the same or another interface 15, usually continuously during the period of the electrophysiological catheter application.

The selected 3D image data, obtained from the extraction, are supplied to the registration module 12 in which the selected 3D image data are correlated with the 3D mapping data provided in step 3 in the correct position and dimension. The 3D mapping data are obtained via a mapping catheter which supplies 3D coordinates of surface points of the heart chamber to be treated via a 6D position sensor integrated into the tip of the catheter. Such catheters are known from the prior art for catheter ablation or, respectively, electroanatomical mapping.

In this process, the catheter is introduced into the respective heart chamber via veins or arteries by the operator. The guidance of the catheter and the recording of the 3D mapping data is not a component part of an embodiment of the present method. During the catheter ablation or the electroanatomical measuring of the heart chamber to be treated, respectively, increasingly more surface points are added to the mapping data in the course of time. These surface points are used for reconstructing the morphological structure of the chamber, i.e. for visualizing it. In this manner, an increasingly more detailed image of the heart chamber to be treated is produced from the electroanatomical 3D mapping data in the course of time.

In the registration step 4 in the registration module 12, the dimensions of the selected 3D image data and of the 3D mapping data are also matched apart from the correlation in the correct position. This is required in order to achieve the best possible matching of the 3D image data of the heart chamber or of its surface in the same orientation, scaling and shape with the corresponding visualization of the heart chamber from the 3D mapping data. As a rule, this requires a transformation of the selected 3D image data or of the 3D mapping data which can comprise three degrees of freedom of translation, three degrees of freedom of rotation, three degrees of freedom of scaling and/or a number of vectors for the deformation.

In a first embodiment, the registration can take place by visual matching. For this purpose, an operator changes the data visualized until the orientation, scaling and/or shape of the heart chamber displayed matches in both representations, i.e. on the basis of the 3D image data and on the basis of the 3D mapping data. The visual matching can take place via a suitable graphical user interface 9.

Furthermore, artificial markers can be used for the registration. In one embodiment, the artificial markers can thus be attached to the chest of the patient before recording the 3D image data. These markers remain fixed at the same position during the entire subsequent catheter application. At least three of these markers are required for achieving correct registration, i.e. correlation of the image data with the mapping data. During this process, markers must be used which are both recognizable in the 3D image data and identifiable by the position sensor of the mapping system.

A further embodiment for registration provides the use of global anatomic markers, i.e. distinct natural points of the area to be treated or its environment, for a registration. These distinct points must be identifiable in the 3D image data and are preferably approached with the mapping catheter by using a fluoroscopic imaging technique. Such distinct points are, for example, the openings of the vena cava superior and inferior or of the coronary sinus. The distinct points can then be detected automatically in the 3D image data and the 3D mapping data so that a correlation of these data with the correct position and dimension can be calculated.

A further advantageous possibility for the registration of the 3D image data and of the 3D mapping data resides in the automatic matching of the surfaces represented on the basis of these data. When the heart chamber to be treated is extracted by way of segmentation, the extracted 3D surface contour of the heart chamber can be automatically matched to the surface contour of the heart chamber obtained by the 3D mapping data. In the case of deviations in the shape of the surface contours obtained from the 3D image data and the 3D mapping data, deforming matching algorithms can be applied to the surface contour from the 3D image data or to the surface contour from the 3D mapping data in order to improve the mutual mapping.

The surface matching can be performed, for example, by reducing or even minimizing point spaces between surface points of the mapping data and surface points of the 3D surface contour extracted from the 3D image data (point-to-point matching). As an alternative, the matching can also be performed by reducing or even minimizing point spaces between surface points of the mapping data and interpolated matching points of the 3D image data (point-to-surface matching).

The surface matching requires a good surface representation by the 3D mapping data of the heart chamber to be treated. However, since these data are collected over a relatively long period of time, as a rule, i.e. only few electroanatomical 3D mapping data are available at the beginning of the catheter ablation, a multi-stage process of the registration is preferably performed. In this process, a registration by a marker takes place in an initial first stage. The accuracy of the registration is then improved in the course of the process by surface matching in a second step.

Naturally, further steps of surface matching, by which a further increase in accuracy is possibly provided, can also be performed with the increasing number of mapping points. This multi-stage registration is of advantage since registration by surface matching, with a correspondingly good surface representation, is more accurate than registration by way of anatomical distinct points or artificial markers, but a good surface representation is only obtained in a later course of an embodiment of the method by the mapping data.

In the initial first stage, a combination of a registration by way of markers and of a registration by way of surface matching can also be effected. Thus, for example, a registration of the left atrium by surface matching of a vessel surface, e.g. of the pulmonary artery, and additionally by way of distinct anatomical points of the right atrium, e.g. of the coronary sinus or of the opening of the vena cava inferior or of the vena cava superior, can be effected.

After the registration between the 3D mapping data and the selected 3D image data, the data are provided in the visualization module 13 in step 5 for the purpose of visualization such that they can be shown in the correct position and dimension next to one another using one or more display units 6. The dashed arrow in the FIGURE indicates the possibility of refining the registration or superimposition during the catheter ablation by means of a multi-stage process as has already been explained above.

For the visualization, different techniques can be used. In one refinement, the selected 3D image data can thus be visualized by way of a volume rendering technique, with the visualization being able to be influenced by adjusting the volume rendering transfer function 7. Since the visualization of the 3D mapping data contains the visualization of the position and orientation of the mapping catheter, it is also possible to superimpose the representation of the position and orientation of the mapping catheter on the selected 3D image data.

In a further embodiment, in the case of segmentation of the 3D image data, the surface extracted from the 3D image data can also be visualized as surface-shaded representation or, after triangulation, as polygonal grid. In this case, too, it is possible to display the position and orientation of the mapping catheter together with the polygonal grid representing the surface.

In one advantageous embodiment of the method, and of the associated device, the two visualizations are linked to one another such that they can be moved, rotated and scaled simultaneously. In addition, a "linked cursor" can be used which shows respective corresponding positions in the visualization of the 3D image data and in the visualization of the 3D mapping data. When the cursor is moved by a user in one of the visualizations, the cursor then moves accordingly in the other visualization.

In addition, the mapping catheter, whose representation is contained in the 3D mapping data and which can be identified in the visualization of these data, as already indicated, can also be overlaid on the visualization of the selected 3D image data when there is appropriate registration between the 3D image data and the 3D mapping data. In this way, the positioning and orientation of this catheter can also be identified at any time in the visualization of the selected 3D image data.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A method for visually supporting an electrophysiology catheter application in a heart of a patient by correlating a 3D surface profile created using 3D image data recorded before the electrophysiology catheter application, with 3D mapping data from a catheter, comprising:

(1) before initiating the electrophysiology catheter application, recording 3D image data for a body region comprising at least part of the heart, the 3D image data being collected using one of computerized tomography (CT) and magnetic resonance tomography (MR);

(2) extracting at least a portion of the heart from said 3D image data, the extracting process comprising segmentation of the 3D image data, and deriving a 3D surface profile comprising at least an area of the heart to be treated from the 3D image data;

(3) after recording the 3D image data, initiating the electrophysiology catheter application with a catheter being inserted into the heart, and a tip of the catheter being moved into contact with a series of different points on surfaces inside the heart including surfaces in the area of the heart to be treated;

wherein the electrophysiology catheter application comprises collecting 3D mapping data using the catheter, the 3D mapping data comprising 3D coordinates of said series of different points on surfaces inside the heart contacted by the tip of the catheter;

wherein ECG gating is used during said collecting of 3D mapping data to ensure that the 3D image data and the 3D mapping data are recorded during a same heart phase;

wherein a plurality of magnetic fields are created outside of the patient, wherein an electromagnetic sensor in the catheter detects said plurality of magnetic fields, and wherein a series of positions of the catheter are determined based on said detection of magnetic fields by the electromagnetic sensor in the catheter;

(4) performing a registration process after the extraction step and while the catheter application is ongoing, the registration process correlating the 3D surface profile created in the extraction step with 3D mapping data, the registration process comprising a first stage and a later in time second stage;

said first stage of the registration process comprising matching anatomical point markers between the 3D surface profile and the 3D mapping data;

wherein fluoroscope imaging is used for imaging the catheter and the heart during the first stage, and wherein fluoroscope imaging is ended when said first stage of the registration process is completed;

said second stage of the registration process comprising surface matching between the 3D surface profile and the 3D mapping data, the surface matching being point-to-surface matching between (i) 3D coordinates of said series of different points inside the heart of the 3D mapping data, and (ii) the 3D surface profile;

wherein more 3D mapping data is available and used in the second stage of the registrations process than in the first stage, with the second stage having greater accuracy than the first stage;

(5) displaying the 3D surface profile and 3D mapping data which has been correlated by the registration process;

wherein a position and orientation of the catheter is also displayed overlaid on said 3D surface profile and said 3D mapping data; and wherein the correlated 3D surface profile and 3D mapping data are linked during display such that rotation, movement, and scaling of one is simultaneously applied to the other.

2. The method as claimed in claim 1, wherein the electrophysiology catheter application comprises cardiac ablation.

3. The method as claimed in claim 1, wherein the 3D image data of the body region are recorded by use of a 3D ultrasonic method.

4. The method as claimed in claim 1, wherein the first stage registration is made automatically using the anatomical points, the anatomical points being identifiable both in the 3D surface profile and in the 3D mapping data.

5. The method as claimed in claim 1, wherein the displaying displays the 3D image data via a volume rendering technique.

6. The method as claimed in claim 5, wherein the displaying displays the 3D surface profile using an adjustable volume rendering transfer function.

7. The method as claimed in claim 1, wherein the displaying displays the 3D surface profile as a polygonal grid.

8. The method as claimed in claim 1,
wherein the 3D image data is collected using computerized tomography (CT).

9. The method as claimed in claim 1, wherein registration between the 3D surface profile and the 3D mapping data prompts the displaying of the position and orientation of the catheter.

10. A device for visually supporting an electrophysiology catheter application by correlating a 3D surface profile created using 3D image data recorded before the electrophysiology catheter application, with 3D mapping data from a catheter:
wherein the device comprises an extraction module comprising at least one processor for executing extraction instructions, a registration module comprising at least one processor for executing registration instructions, a 3D image data input interface, an ECG, a fluoroscope, a catheter, and a display;
wherein the device is configured to support the electrophysiology catheter applications as follows:
(1) the input interface is configured to receive 3D image data for a body region comprising at least part of the heart, the 3D image data comprising at least one of computerized tomography (CT) and magnetic resonance tomography (MR) data;
(2) the extraction module being configured to extract at least portions of the heart from 3D image data received by the input interface, the extracting process comprising segmentation of the 3D image data, and deriving a 3D surface profile comprising at least an area of the heart to be treated from the 3D image data;
(3) the device being configured to receive 3D mapping data from the catheter during the electrophysiology catheter application and after recording the 3D image data, and to simultaneously receive ECG signals from the ECG;
wherein the 3D mapping data comprises 3D coordinates of a series of different points on surfaces inside the heart when the heart is contacted by the tip of the catheter;
wherein an electromagnetic sensor of the catheter is adapted to detect a plurality of magnetic fields, and wherein the device is configured to determine the 3D coordinates of the series of different points based on said plurality of magnetic fields detected by the electromagnetic sensor of the catheter;
the device being configured to use ECG signals received from the ECG interface for ECG gating during said collecting of 3D mapping data to ensure that the 3D image data and the 3D mapping data are recorded during a same heart phase;
(4) the registration module being configured to perform a registration process after the extraction module has provided said 3D surface profile and while 3D mapping data is received from the catheter, the registration process correlating the 3D surface profile with 3D mapping data, the registration process comprising a first stage and a later in time second stage, with more 3D mapping data being available for the second stage than for the first stage;
said first stage of the registration process comprising matching anatomical point markers between the 3D surface profile and the 3D mapping data;
the device being configured to display fluoroscope images of the catheter and the heart on the display during the first stage of the registration process, and to end fluoroscope imaging when the first stage of registration is completed;
said second stage of the registration process comprising surface matching between the 3D surface profile and the 3D mapping data, the surface matching being point-to-surface matching between (i) 3D coordinates of said series of different points inside the heart of the 3D mapping data, and (ii) the 3D surface profile;
(5) wherein the display is configured to display the 3D surface profile and 3D mapping data, received from the registration module, which have been correlated by the registration process;
the device being configured to display a position and orientation of the catheter overlaid on said 3D surface profile data and said 3D mapping data;
the device being configured to link the correlated 3D surface profile and 3D mapping data on the display such that rotation, movement, and scaling of one is simultaneously applied to the other.

11. The device as claimed in claim 10, wherein the catheter is an ablation catheter.

12. The device as claimed in claim 10,
further comprising a plurality of magnetic field generators positioned under a patient table and configured to generate said plurality of magnetic fields to be detected by the electromagnetic sensor of the catheter.

13. The device as claimed in claim 10,
wherein the device comprises a display module, the display module comprising said display;
wherein the display module is configured such that when a user rotates, moves or scales one of the displayed 3D surface profile and the 3D mapping data, the other is simultaneously subjected to the same rotation, movement or scaling on the display.

14. The method of claim 1:
wherein a plurality of magnetic field generators are provided under a patient table; and
wherein said plurality of magnetic fields are created by the magnetic field generators, and said series of positions of the catheter are determined based on said detection of magnetic fields by the electromagnetic sensor in the catheter.

* * * * *